United States Patent
Beavers et al.

(10) Patent No.: US 7,902,191 B2
(45) Date of Patent: Mar. 8, 2011

(54) HISTAMINE H3 RECEPTOR ANTAGONISTS, PREPARATION AND THERAPEUTIC USES

(75) Inventors: Lisa Selsam Beavers, Franklin, IN (US);
Robert Alan Gadski, Indianapolis, IN (US); Philip Arthur Hipskind, New Palestine, IN (US); Cynthia Darshini Jesudason, Indianapolis, IN (US); Karen Lynn Lobb, Indianapolis, IN (US); Richard Todd Pickard, Noblesville, IN (US); Craig William Lindsley, Schwenksville, PA (US)

(73) Assignee: Eli Lilly and Company, Indianapolis, IN (US)

( * ) Notice: Subject to any disclaimer, the term of this patent is extended or adjusted under 35 U.S.C. 154(b) by 1166 days.

(21) Appl. No.: 10/598,262

(22) PCT Filed: Feb. 22, 2005

(86) PCT No.: PCT/US2005/005491
§ 371 (c)(1),
(2), (4) Date: Aug. 23, 2006

(87) PCT Pub. No.: WO2005/082893
PCT Pub. Date: Sep. 9, 2005

(65) Prior Publication Data
US 2007/0155754 A1 Jul. 5, 2007

Related U.S. Application Data

(60) Provisional application No. 60/547,758, filed on Feb. 25, 2004.

(51) Int. Cl.
| | |
|---|---|
| *A01N 43/40* | (2006.01) |
| *A61K 31/445* | (2006.01) |
| *A61K 31/497* | (2006.01) |
| *A61K 31/535* | (2006.01) |
| *C07D 207/00* | (2006.01) |
| *C07D 211/06* | (2006.01) |
| *C07D 295/00* | (2006.01) |
| *C07D 403/00* | (2006.01) |
| *C07D 413/00* | (2006.01) |

(52) U.S. Cl. ............ 514/235.5; 514/252.13; 514/254.01; 514/319; 514/422; 544/141; 544/372; 546/205; 548/518

(58) Field of Classification Search .............. 514/235.5, 514/254.01, 252.13, 422, 319; 544/141, 544/372; 546/205; 548/518
See application file for complete search history.

(56) References Cited

FOREIGN PATENT DOCUMENTS
| | | | |
|---|---|---|---|
| EP | 0 375 297 | * | 6/1990 |
| FR | 1 494 630 | | 9/1967 |
| GB | 276571 | * | 9/1927 |
| GB | 840 358 | | 7/1960 |
| WO | WO 02/076925 | | 10/2002 |
| WO | WO 03/064411 | | 8/2003 |

OTHER PUBLICATIONS

Ferrari, et al., New Series of b-adrenergic blocking agents, Bollettino Chimico Farmaceutico 103(1), 32-6 (1964).*
Fujimura, et al., Syntheses and Pharmacological Action of Tetralin Derivatives, Yakugaku Zasshi, 74, 954-6 (1954).*
Hancock, et al., Antiobesity Effects of A-331440, a Novel Non-imidazole Histamine H Receptor Antagonist, European J. of Pharm., 487, 183-197 (2004).*
Fujimura et al., "Syntheses and pharmacological action of Tetralin derivates," *Yakugaku Zasshi—Journal of the Pharmaceutical Society of Japan*, No. 74, pp. 954-956, 1954.

* cited by examiner

*Primary Examiner* — James O Wilson
*Assistant Examiner* — Erich A Leeser
(74) *Attorney, Agent, or Firm* — Dan L. Wood

(57) ABSTRACT

The present invention discloses novel compounds of Formula I or pharmaceutically acceptable salts thereof which have histamine-H3 receptor antagonist activity as well as methods for preparing such compounds. In another embodiment, the invention discloses pharmaceutical compositions comprising compounds of Formula I as well as methods of using them to treat obesity and other histamine H3 receptor-related diseases.

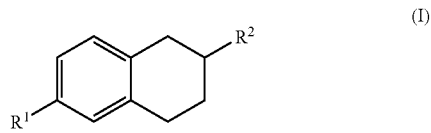

4 Claims, No Drawings

HISTAMINE H3 RECEPTOR ANTAGONISTS, PREPARATION AND THERAPEUTIC USES

This is the national phase application, under 35 U.S.C. 371, for PCT International Application No. PCT/US2005/005,491 filed 22 Feb. 2005, which claims the benefit under 35 U.S.C. 119(e) to U.S. Provisional Application No. 60/547,758 filed 25 Feb. 2004.

The present invention relates to histamine H3 receptor antagonists, and as such are useful in the treatment of disorders responsive to the inactivation of histamine H3 receptors, such as obesity, cognitive disorders, attention deficit disorders, and the like.

The histamine H3 receptor (H3R) is a presynaptic autoreceptor and hetero-receptor found in the peripheral and central nervous system and regulates the release of histamine and other neurotransmitters, such as serotonin and acetylcholine. This is an example of an H3 receptor mediated cellular response. Recent evidence suggests that the H3 receptor shows intrinsic, constitutive activity, in vitro as well as in vivo (i.e. it is active in the absence of an agonist). Compounds acting as inverse agonists can inhibit this activity. A histamine H3 receptor antagonist or inverse agonist would therefore be expected to increase the release of H3 receptor-regulated neurotransmitters in the brain. A histamine H3 receptor agonist, on the contrary, leads to an inhibition of the biosynthesis of histamine and an inhibition of the release of histamine and also of other neurotransmitters such as serotonin and acetylcholine. The histamine H3 receptor is relatively neuron specific and inhibits the release of a number of monamines, including histamine. Selective antagonism of the histamine H3 receptor raises brain histamine levels and inhibits such activities as food consumption while minimizing non-specific peripheral consequences. Antagonists of the histamine H3 receptor increase synthesis and release of cerebral histamine and other monoamines. By this mechanism, they induce a prolonged wakefulness, improved cognitive function, reduction in food intake and normalization of vestibular reflexes. Accordingly, the histamine H3 receptor is an important target for new therapeutics in Alzheimer disease, mood and attention adjustments, cognitive deficiencies, obesity, dizziness, schizophrenia, epilepsy, sleeping disorders, narcolepsy and motion sickness.

The majority of histamine H3 receptor antagonists to date resemble histamine in possessing an imidazole ring generally substituted in the 4(5) position (Ganellin et al., Ars Pharmaceutica, 1995, 36:3, 455-468). A variety of patents and patent applications directed to antagonists and agonists having such structures include EP 197840, EP 494010, WO 97/29092, WO 96/38141, and WO 96/38142. These imidazole-containing compounds have the disadvantage of poor blood-brain barrier penetration, interaction with cytochrome P-450 proteins, and hepatic and ocular toxicities.

Non-imidazole neuroactive compounds such as beta histamines (Arrang, Eur. J. Pharm. 1985, 111:72-84) demonstrated some histamine H3 receptor activity but with poor potency. EP 978512 published Mar. 1, 2000 discloses non-imidazole aryloxy alkylamines histamine H3 receptor antagonists but does not disclose the affinity, if any, of these antagonists for recently identified histamine receptor GPRv53, described below. EP 0982300A2 (pub. Mar. 1, 2000) discloses non-imidazole alkyamines as histamine HS receptor ligands. The subject invention is distinct from EP 0982300A2 in the structure and activities of the present compounds.

Histamine mediates its activity via four receptor subtypes, H1R, H2R, H3R and a newly identified receptor designated GPRv53 [(Oda T., et al., J. Biol. Chem. 275 (47): 36781-6 (2000)]. Although relatively selective ligands have been developed for H1R, H2R and H3R, few specific ligands have been developed that can distinguish H3R from GPRv53. GPRv53 is a widely distributed receptor found at high levels in human leukocytes. Activation or inhibition of this receptor could result in undesirable side effects when targeting antagonism of the H3R receptor. Furthermore, the identification of this new receptor has fundamentally changed histamine biology and must be considered in the development of histamine H3 receptor antagonists.

Because of the unresolved deficiencies of the compounds described above, there is a continuing need for improved methods and compositions to treat disorders associated with histamine H3 receptors.

The present invention provides compounds that are useful as histamine H3 receptor antagonists. In another aspect, the present invention provides compounds that are useful as selective antagonists of the histamine H3 receptor but have little or no binding affinity of GPRv53. In another aspect the present invention includes methods of making the compounds of Formula I or II or III. In yet another aspect, the present invention provides pharmaceutical compositions comprising antagonists of the histamine H3 receptor.

In yet another aspect, the present invention provides compounds, pharmaceutical compositions, and methods useful in the treatment of obesity, cognitive disorders, attention deficit disorders and other disorders associated with histamine H3 receptor.

The present invention is a compound structurally represented by Formula I;

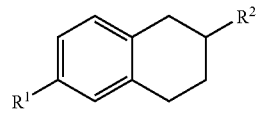

or pharmaceutically acceptable salts thereof wherein:

$R^1$ is

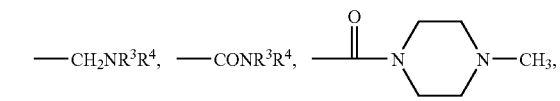

$R^2$ is

— Hydrogen,
— NH—($C_1$-$C_6$) alkyl,
— NH—($C_1$-$C_4$) alkylene-phenyl,
— NH($C_3$-$C_6$) cycloakyl,
— $NR^3R^4$ —N(piperazine)N—CH$_3$, —N(piperidine), —N(pyrrolidine), wherein;
$R^3$ is hydrogen,
—($C_1$-$C_4$) alkyl,
$R^4$ is
—($C_1$-$C_4$) alkyl,
—($C_1$-$C_4$) alkylene-phenyl,
wherein $R^3$ and $R^4$ can cyclize to form, together with the nitrogen to which they are attached, a five or six-membered ring, wherein optionally one of the carbons of the ring formed by said nitrogen, $R^3$, and $R^4$, is replaced by a nitrogen or oxygen, and wherein said ring is optionally further substituted by $R^5$, and
$R^5$ is hydrogen,
—($C_1$-$C_4$) alkyl, wherein optionally $R^5$ forms a three to five membered ring with the nitrogen containing ring to which it is attached,
—($C_1$-$C_4$) alkylene-N-pyrrolidinyl,
—($C_1$-$C_4$) alkylene-N-piperidinyl.

While all of the compounds of the present invention are useful, certain of the compounds are particularly interesting and are preferred. The following listing sets out several groups of preferred compounds. It will be understood that each of the listings may be combined with other listings to create additional groups of preferred embodiments.

1. The compound of Formula I, wherein $R^1$ is $CONR^3R^4$, and $R^3$ and $R^4$ cyclize to form, together with the nitrogen to which they are attached, a five membered ring, and said ring is further substituted by —CH$_2$— pyrrolidinyl.
2. The compound of Formula I, wherein $R^1$ is $CH_2NR^3R^4$, and $R^3$ and $R^4$ cyclize to form, together with the nitrogen to which they are attached, a five membered ring, and said ring is further substituted by —CH$_2$— pyrrolidinyl.
3. The compound of Formula I wherein $R^2$ is $NR^3R^4$, and $R^3$ and $R^4$ cyclize to form, together with the nitrogen to which they are attached, a five membered ring.
4. The compound of Formula I wherein $R^2$ is $NR^3R^4$, and $R^3$ and $R^4$ cyclize to form, together with the nitrogen to which they are attached, a five membered ring.

5. A compound of Formula II (II)

wherein Z is -carbonyl-, or —CH$_2$—.

6. A compound of Formula III (III)

The present invention is a pharmaceutical composition which comprises a compound of Formula I or II or III and a pharmaceutically acceptable carrier. Pharmaceutical formulations of Formula I or II or III can provide a method of selectively increasing histamine levels in cells by contacting the cells with an antagonist of the histamine H3 receptor, the antagonists being a compound of Formula I or II or III. Thus, the methods of this invention encompass a prophylactic and therapeutic administration of a compound of Formula I or II or III.

The present invention further provides an antagonist of Formula I or II or III which is characterized by having little or no binding affinity for the histamine receptor GPRv53. Thus, a pharmaceutical preparation of Formula I or II or III can be useful in the treatment or prevention of obesity, cognitive disorders, attention deficit disorders and the like, which comprises administering to a subject in need of such treatment or prevention an effective amount of a compound of Formula I or II or III. In addition, a pharmaceutical preparation of Formula I or II or III can be useful in the treatment or prevention of a disorder or disease in which inhibition of the histamine H3 receptor has a beneficial effect or the treatment or prevention of eating disorders which comprises administering to a subject in need of such treatment or prevention an effective amount of a compound of Formula I or II or III.

DETAILED DESCRIPTION OF THE INVENTION

General terms used in the description of compounds, compositions, and methods herein described, bear their usual meanings. Throughout the instant application, the following terms have the indicated meanings:

The term "GPRv53" means a recently identified novel histamine receptor as described in Oda, et al., supra. Alternative names for this receptor are PORT3 or H4R.

The term "H3R" means to the histamine H3 receptor that inhibits the release of a number of monoamines, including histamine.

The term "H1R" means to the histamine H1 receptor subtype.

The term "H2R" means to the histamine H2 receptor subtype.

The term "selective H3R antagonists" is defined as the ability of a compound of the present invention to block forskolin-stimulated cAMP production in response to agonist R (–)α methylhistamine.

In the general formulae of the present document, the general chemical terms have their usual meanings. For example:

"Alkylene" are a saturated hydrocarbyldiyl radical of straight or branched configuration made up of from 1 to 4 carbon atoms. Included within the scope of this term are methylene, 1,2-ethane-diyl, 1,1-ethane-diyl, 1,3-propane diyl, 1,2-propane diyl, 1,3 butane-diyl, 1,4-butane diyl, and the like.

"$C_3$-$C_7$ cycloalkylene" are a saturated hydrocarbyldiyl radical of cyclic configuration, optionally branched, made up of from 3 to 7 carbon atoms. Included within the scope of this term are cyclopropyl, cyclobutyl, cyclopentyl and cyclohexyl, and the like.

"Alkyl" are one to six carbon atoms such as methyl, ethyl, propyl, butyl, pentyl, hexyl, and the like, and isomeric forms thereof.

"Aryl" are six to twelve carbon atoms such as phenyl, alpha-naphthyl, beta-naphthyl, m-methylphenyl, p-trifluoromethylphenyl and the like. The aryl groups can also be substituted with one to 3 hydroxy, fluoro, chloro, or bromo groups.

"Cycloalkyl" are three to six carbon atoms such as cyclopropyl, cyclobutyl, cyclopentyl and cyclohexyl, and the like.

"—($C_1$-$C_4$) alkylene-N-pyrrolidinyl" is;

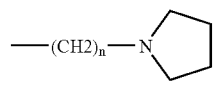

wherein n=1-4

"—($C_1$-$C_4$) alkylene-N-piperidinyl" is;

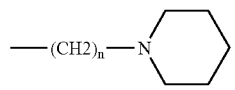

wherein n=1-4

"Halogen" or "halo" means fluoro, chloro, bromo and iodo.

"Composition" means a pharmaceutical composition and is intended to encompass a pharmaceutical product comprising the active ingredient(s), Formula I or II or III, and the inert ingredient(s) that make up the carrier. Accordingly, the pharmaceutical compositions of the present invention encompass any composition made by admixing a compound of the present invention and a pharmaceutically acceptable carrier.

The term "unit dosage form" means physically discrete units suitable as unitary dosages for human subjects and other non-human animals, each unit containing a predetermined quantity of active material calculated to produce the desired therapeutic effect, in association with a suitable pharmaceutical carrier.

The terms "treating" and "treat," as used herein, include their generally accepted meanings, i.e., preventing, prohibiting, restraining, alleviating, ameliorating, slowing, stopping, or reversing the progression or severity of a pathological condition, described herein.

The invention includes tautomers, enantiomers and other stereoisomers of the compounds also. Thus, as one skilled in the art knows, certain aryls may exist in tautomeric forms. Such variations are contemplated to be within the scope of the invention. It will be understood that, as used herein, references to the compounds of Formula I or II or III are meant to also include the pharmaceutical salts, its enantiomers and racemic mixtures thereof.

As used herein, the term "stereoisomer" refers to a compound made up of the same atoms bonded by the same bonds but having different three-dimensional structures which are not interchangeable. The three-dimensional structures are called configurations. As used herein, the term "enantiomer" refers to two stereoisomers whose molecules are nonsuperimposable mirror images of one another. The term "chiral center" refers to a carbon atom to which four different groups are attached. As used herein, the term "diastereomers" refers to stereoisomers which are not enantiomers. In addition, two diastereomers which have a different configuration at only one chiral center are referred to herein as "epimers." The terms "racemate," "racemic mixture" or "racemic modification" refer to a mixture of equal parts of enantiomers.

The term "enantiomeric enrichment" as used herein refers to the increase in the amount of one enantiomer as compared to the other. A convenient method of expressing the enantiomeric enrichment achieved is the concept of enantiomeric excess, or "ee," which is found using the following equation:

$$ee = \frac{E^1 - E^2}{E^1 + E^2} \times 100$$

wherein $E^1$ is the amount of the first enantiomer and $E^2$ is the amount of the second enantiomer. Thus, if the initial ratio of the two enantiomers is 50:50, such as is present in a racemic mixture, and an enantiomeric enrichment sufficient to produce a final ratio of 70:30 is achieved, the ee with respect to the first enantiomer is 40%. However, if the final ratio is 90:10, the ee with respect to the first enantiomer is 80%. An ee of greater than 90% is preferred, an ee of greater than 95% is most preferred and an ee of greater than 99% is most especially preferred. Enantiomeric enrichment is readily determined by one of ordinary skill in the art using standard techniques and procedures, such as gas or high performance liquid chromatography with a chiral column. Choice of the appropriate chiral column, eluent and conditions necessary to effect separation of the enantiomeric pair is well within the knowledge of one of ordinary skill in the art. In addition, the specific stereoisomers and enantiomers of compounds of Formula I or II or III can be prepared by one of ordinary skill in the art utilizing well known techniques and processes, such as those disclosed by J. Jacques, et al., "*Enantiomers, Racemates, and Resolutions,*" John Wiley and Sons, Inc., 1981, and E. L. Eliel and S. H. Wilen, "*Stereochemistry of Organic Compounds,*" (Wiley-Interscience 1994), and European Patent Application No. EP-A-838448, published Apr. 29, 1998. Examples of resolutions include recrystallization techniques or chiral chromatography.

Some of the compounds of the present invention have one or more chiral centers and may exist in a variety of stereoisomeric configurations. As a consequence of these chiral centers, the compounds of the present invention occur as racemates, mixtures of enantiomers and as individual enantiomers, as well as diastereomers and mixtures of diastereomers. All such racemates, enantiomers, and diastereomers are within the scope of the present invention.

The terms "R" and "S" are used herein as commonly used in organic chemistry to denote specific configuration of a chiral center. The term "R" (rectus) refers to that configuration of a chiral center with a clockwise relationship of group priorities (highest to second lowest) when viewed along the bond toward the lowest priority group. The term "S" (sinister) refers to that configuration of a chiral center with a counter-clockwise relationship of group priorities (highest to second lowest) when viewed along the bond toward the lowest priority group. The priority of groups is based upon their atomic number (in order of decreasing atomic number). A partial list of priorities and a discussion of stereochemistry is contained in "Nomenclature of Organic Compounds: Principles and Practice," (J. H. Fletcher, et al., eds., 1974) at pages 103-120.

The designation " ▬ " refers to a bond that protrudes forward out of the plane of the page. The designation " ''''''' " refers to a bond that protrudes backward out of the plane of the page. The designation " ⁓⁓ " refers to a bond wherein the stereochemistry is not defined.

In general, the term "pharmaceutical" when used as an adjective means substantially non-toxic to living organisms. For example, the term "pharmaceutical salt" as used herein, refers to salts of the compounds of Formula I or II or III which are substantially non-toxic to living organisms. See, e.g., Berge, S. M, Bighley, L. D., and Monkhouse, D. C., "Pharmaceutical Salts," J. Pharm. Sci., 66:1, 1977. Typical pharmaceutical salts include those salts prepared by reaction of the compounds of Formula I or II or III with an inorganic or organic acid or base. Such salts are known as acid addition or base addition salts respectively. These pharmaceutical salts frequently have enhanced solubility characteristics compared to the compound from which they are derived, and thus are often more amenable to formulation as liquids or emulsions.

The term "acid addition salt" refers to a salt of a compound of Formula I or II or III prepared by reaction of a compound of Formula I or II or III with a mineral or organic acid. For exemplification of pharmaceutical acid addition salts see, e.g., Berge, S. M, Bighley, L. D., and Monkhouse, D. C., J. Pharm. Sci., 66:1, 1977. Since compounds of this invention can be basic in nature, they accordingly react with any of a number of inorganic and organic acids to form pharmaceutical acid addition salts.

The pharmaceutical acid addition salts of the invention are typically formed by reacting the compound of Formula I or II or III with an equimolar or excess amount of acid. The reactants are generally combined in a mutual solvent such as diethylether, tetrahydrofuran, methanol, ethanol, isopropanol, benzene, and the like. The salts normally precipitate out of solution within about one hour to about ten days and can be isolated by filtration or other conventional methods.

Acids commonly employed to form acid addition salts are inorganic acids such as hydrochloric acid, hydrobromic acid, hydroiodic acid, sulfuric acid, phosphoric acid, and the like, and acids commonly employed to form such salts are inorganic acids such as hydrochloric acid, hydrobromic acid, hydroiodic acid, sulfuric acid, phosphoric acid, and the like, and organic acids, such as p-toluenesulfonic acid, methanesulfonic acid, oxalic acid, p-bromophenylsulfonic acid, carbonic acid, succinic acid, citric acid, benzoic acid, acetic acid and the like. Examples of such pharmaceutically acceptable salts thus are the sulfate, pyrosulfate, bisulfate, sulfite, bisulfite, phosphate, monohydrogenphosphate, dihydrogenphosphate, metaphosphate, pyrophosphate, chloride, bromide, iodide, acetate, propionate, decanoate, caprylate, acrylate, formate, isobutyrate, caproate, heptanoate, propiolate, oxalate, malonate, succinate, suberate, sebacate, fumarate, maleate, butyne-1,4-dioate, hexyne-1,6-dioate, benzoate, chlorobenzoate, methylbenzoate, dinitrobenzoate, hydroxybenzoate, methoxybenzoate, phthalate, sulfonate, xylenesulfonate, phenylacetate, phenylpropionate, phenylbutyrate, citrate, lactate, β-hydroxybutyrate, glycollate, tartrate, methanesulfonate, propanesulfonate, naphthalene-1-sulfonate, naphthalene-2-sulfonate, mandelate and the like.

The term "base addition salt" refers to a salt of a compound of Formula I or II or III prepared by reaction of a compound of Formula I or II or III with a mineral or organic base. For exemplification of pharmaceutical base addition salts see, e.g., Berge, S. M, Bighley, L. D., and Monkhouse, D. C., J. Pharm. Sci., 66:1, 1977. This invention also contemplates pharmaceutical base addition salts of compounds of Formula I or II or III. The skilled artisan would appreciate that some compounds of Formula I or II or III may be acidic in nature and accordingly react with any of a number of inorganic and organic bases to form pharmaceutical base addition salts. Examples of pharmaceutical base addition salts are the ammonium, lithium, potassium, sodium, calcium, magnesium, methylamine, diethyl amino, ethylene diamino, cyclohexylamino, and ethanolamino salts, and the like of a compound of Formula I or II or III.

The compounds of Formula I or II or III, when existing as a diastereomeric mixture, may be separated into diastereomeric pairs of enantiomers by, for example, fractional crystallization from a suitable solvent, for example methanol or ethyl acetate or a mixture thereof. The pair of enantiomers thus obtained may be separated into individual stereoisomers by conventional means, for example by the use of an optically active acid as a resolving agent. Alternatively, any enantiomer of a compound of the formula may be obtained by stereospecific synthesis using optically pure starting materials or reagents of known configuration or through enantioselective synthesis.

The compounds of Formula I or II or III can be prepared by one of ordinary skill in the art following a variety of procedures, some of which are illustrated in the procedures and schemes set forth below. The particular order of steps required to produce the compounds of Formula I or II or III is dependent upon the particular compound to being synthesized, the starting compound, and the relative liability of the substituted moieties. The reagents or starting materials are readily available to one of skill in the art, and to the extent not commercially available, are readily synthesized by one of ordinary skill in the art following standard procedures commonly employed in the art, along with the various procedures and schemes set forth below.

The following Preparations and Examples are provided to better elucidate the practice of the present invention and should not be interpreted in any way as to limit the scope of the same. Those skilled in the art will recognize that various modifications may be made while not departing from the spirit and scope of the invention. All publications mentioned in the specification are indicative of the level of those skilled in the art to which this invention pertains.

The terms and abbreviations used in the instant Preparations and Examples have their normal meanings unless otherwise designated. For example, as used herein, the following terms have the meanings indicated: "eq" refers to equivalents; "N" refers to normal or normality, "M" refers to molar or molarity, "g" refers to gram or grams, "mg" refers to milligrams; "L" refers to liters; "mL" refers to milliliters; "µL" refers to microliters; "mol" refers to moles; "mmol" refers to millimoles; "psi" refers to pounds per square inch; "min" refers to minutes; "h" or "hr" refers to hours; "° C." refers to degrees Celsius; "TLC" refers to thin layer chromatography; "HPLC" refers to high performance liquid chromatography; "$R_f$" refers to retention factor; "$R_t$" refers to retention time; "δ" refers to part per million down-field from tetramethylsilane; "MS" refers to mass spectrometry, Observed Mass indicates (M+1) unless indicated otherwise. "MS(FD)" refers to field desorption mass spectrometry, "MS(IS)" refers to ion spray mass spectrometry, "MS(FIA)" refers to flow injection analysis mass spectrometry, "MS(FAB)" refers to fast atom bombardment mass spectrometry, "MS(EI)" refers to electron impact mass spectrometry, "MS(ES)" refers to electron spray mass spectrometry, "MS(APCI)" refers to atmospheric pressure chemical ionization mass spectrometry. "UV" refers to ultraviolet spectrometry, "$^1$H NMR" refers to proton nuclear magnetic resonance spectrometry. In addition, "IR" refers to infra red spectrometry, and the absorption maxima listed for the IR spectra are only those of interest and not all of the maxima observed. "RT" refers to room temperature.

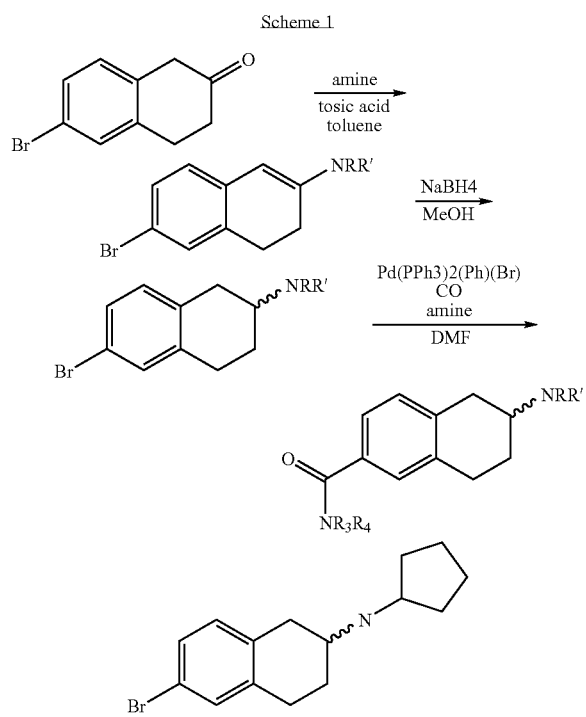

Preparation 1

(6-bromo-1,2,3,4-tetrahydro-naphthalen-2-yl)-cyclopentyl-amine

Charged 50 mL round bottomed flask with 6-bromo-2-tetralone (0.750 g., 3.33 mmoles., 1.0 eq.), cylcopentylamine (0.567 g., 0.648 mL., 6.66 mmoles., 2.0 eq.) and catalytic amount of tosic acid. Fitted flask with a Dean-Stark trap and heated reaction mixture overnight at 155° C. The next day, removed remaining solvent from reaction mixture using reduced pressure. Added 25 mL of methanol and placed reaction mixture on an ice bath. Added sodium borohydride (0.630 g, 16.6 mmoles, 5.0 eq.). Removed ice bath and allowed to stir for several hours. Partitioned reaction mixture between ethyl acetate and 1.0 N HCl aqueous solution. Extracted organic layer two times more with 1.0 N HCl solution. Combined acidic extractions and basified with 5.0 N NaOH. Extracted basic aqueous with methylene chloride three times. Combined organic extracts and dried over Na$_2$SO$_4$. Removed solvents using reduced pressure to obtain 0.429 g. (crude yield=43%). Purified using a reverse phase column and acetonitrile:TFA buffer solvent gradient. Collected TFA salt of 6-bromo-1,2,3,4-tetrahydro-naphthalen-2-yl)-cyclopentyl-amine. Partitioned the product between methylene chloride and 2.0N sodium carbonate solution. Washed organic layer with 2.0N sodium carbonate a second time and then with brine. Dried organic layer over sodium sulfate and removed solvent via reduced pressure to obtain 0.324 g. (yield=33%). Mass spectrum (APCI): 294 (M$^+$+1).

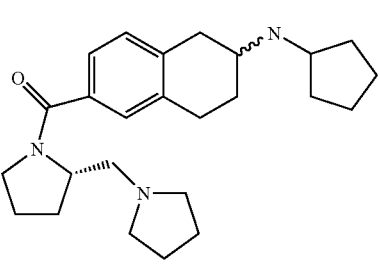

Example 1

Synthesis of (6-Cyclopentyl amino-5,6,7,8-tetrahydro-naphthalen-2-yl)-(2-pyrrolidin-1-ylmethyl-pyrrolidin-1-yl)-methanone Procedure A: Charged 10 mL round bottomed flask with 6-bromo-1,2,3,4-tetrahydro-naphthalen-2-yl)-cyclopentyl-amine (0.200 g, 0.678 mmoles, 1.0 eq.); (S)-(+)-1-(2-pyrrolidinylmethyl)pyrrolidinone (0.152 g., 0.986 mmoles., 1.45 eq.); tri-n-butylamine (0.138 g., 0.748 mmoles., 1.10 eq.); 1 mL DMF; and trans-dibromobis(triphenylphosphine)palladium (II) (8.1 mg., 0.010 mmoles., 0.015 eq.). Flushed reaction flask with carbon monoxide. Heated reaction mixture under a carbon monoxide balloon at 85° C. overnight. The next day, partitioned the reaction mixture between ethyl ether and water. Extracted water layer two times more with ethyl ether. Washed the combined organic extracts with brine. Dried organic extracts over sodium sulfate and removed solvents under reduced pressure to obtain 150.1 mg. (crude yield=56%) Submitted for reverse phase chromatography using Waters Xterra MS C18 5 uM 19×100 mm column and acetonitrile and 5 mM aqueous sodium carbonate buffer solvent system. Obtained 44.1 mg. (yield=16%). Mass spectrum (APCI): 396 (M$^+$+1).

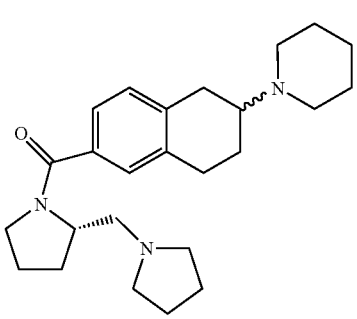

Example 2

(6-Piperidin-1-yl-5,6,7,8-tetrahydro-naphthalen-2-yl)-(2-pyrrolidin-1-ylmethyl-pyrrolidin-1-yl)-methanone is prepared from 1-(6-bromo-1,2,3,4-tetrahydro-naphthalen-2-yl)-

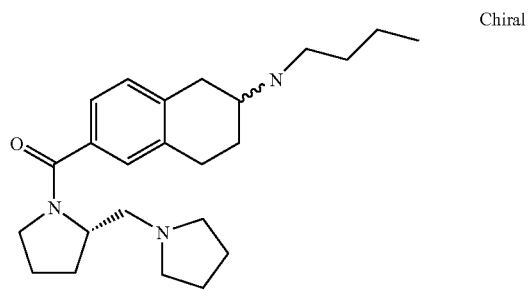

Example 5

(6-Butylamino-5,6,7,8-tetrahydro-naphthalen-2-yl)-(2-pyrrolidin-1-ylmethyl-pyrrolidin-1-yl)-methanone is prepared from (6-bromo-1,2,3,4-tetrahydro-naphthalen-2-yl)-butyl-amine and (S)-(+)-1-(2-pyrrolidinylmethyl)-pyrrolidine in a manner substantially analogous to Procedure A. (See herein Example 1). Starting material, (6-bromo-1,2,3,4-tetrahydro-naphthalen-2-yl)-butyl-amine, was prepared from 6-bromo-2-tetralone and n-butylamine in a manner substantially analogous to Preparation 1. Mass spectrum (APCI) 384 ($M^+$+1).

piperidine and (S)-(+)-1-(2-pyrrolidinylmethyl)-pyrrolidine in a manner substantially analogous to Procedure A. (See herein Example 1). Starting material, (6-bromo-1,2,3,4-tetrahydro-naphthalen-2-yl)-piperidine, was prepared from 6-bromo-2-tetralone and piperidine in a manner substantially analogous to Preparation 1. Mass Spectrum (ES+) 396.

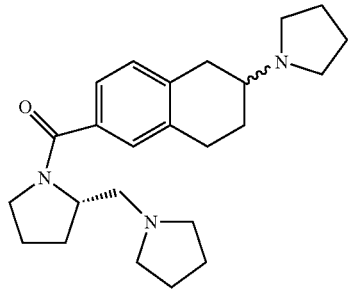

Example 3

(2-Pyrrolidin-1-ylmethyl-pyrrolidin-1-yl)-(6-pyrrolidin-1-yl-5,6,7,8-tetrahydro-naphthalen-2-yl)-methanone is prepared from 1-(6-bromo-1,2,3,4-tetrahydro-naphthalen-2-yl)-pyrrolidine and (S)-(+)-1-(2-pyrrolidinylmethyl)-pyrrolidine in a manner substantially analogous to Procedure A. (See herein Example 1). Starting material, (6-bromo-1,2,3,4-tetrahydro-naphthalen-2-yl)-pyrrolidine, was prepared from 6-bromo-2-tetralone and pyrrolidine in a manner substantially analogous to Preparation 1. Mass Spectrum (APCI) 382 ($M^+$+1).

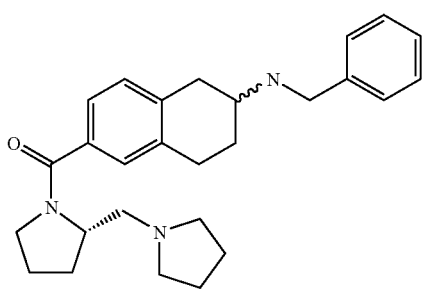

Example 4

(6-Benzylamino-5,6,7,8-tetrahydro-naphthalen-2-yl)-(2-pyrrolidin-1-ylmethyl-pyrrolidin-1-yl)-methanone is prepared from benzyl-(6-bromo-1,2,3,4-tetrahydro-naphthalen-2-yl)-amine and (S)-(+)-1-(2-pyrrolidinylmethyl)-pyrrolidine in a manner substantially analogous to Procedure A. (See herein Example 1). Starting material, benzyl-(6-bromo-1,2,3,4-tetrahydro-naphthalen-2-yl)-amine, can be prepared from 6-bromo-2-tetralone and benzylamine in a manner substantially analogous to Preparation 1. Mass spectrum (APCI) 418 ($M^+$+1).

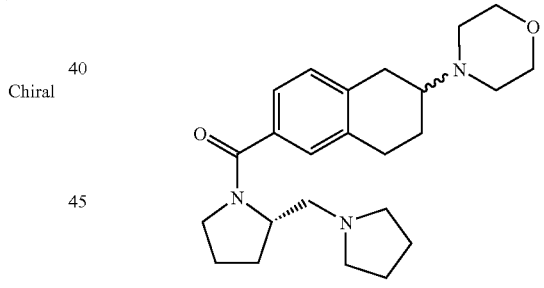

Example 6

(6-Morpholin-4-yl-5,6,7,8-tetrahydro-naphthalen-2-yl)-(2-pyrrolidin-1-ylmethyl-pyrrolidin-1-yl)-methanone is prepared from 4-(6-bromo-1,2,3,4-tetrahydro-naphthalen-2-yl)-morpholine and (S)-(+)-1-(2-pyrrolidinylmethyl)-pyrrolidine in a manner substantially analogous to Procedure A. (See herein Example 1). Starting material, 4-(6-bromo-1,2,3,4-tetrahydro-naphthalen-2-yl)-morpholine, was prepared from 6-bromo-2-tetralone and morpholine in a manner substantially analogous to Preparation 1. Mass spectrum (APCI): 389 ($M^+$+1).

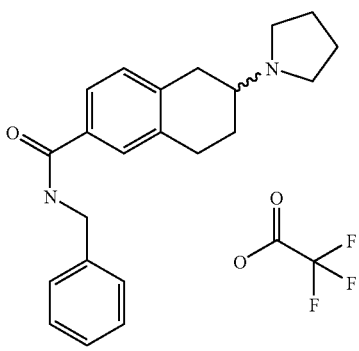

Example 7

6-Pyrrolidin-1-yl-5,6,7,8-tetrahydro-naphthalene-2-carboxylic acid benzylamide; compound with trifluoro-acetic acid is prepared from 1-(6-bromo-1,2,3,4-tetrahydro-naphthalen-2-yl)-pyrrolidine and benzylamine in a manner substantially analogous to Procedure A except reverse phase purification used TFA buffer instead of sodium carbonate buffer. (See herein Example 1). Starting material, 1-(6-bromo-1,2,3,4-tetrahydro-naphthalen-2-yl)-pyrrolidine, was prepared from 6-bromo-2-tetralone and pyrrolidine in a manner substantially analogous to Preparation 1. Mass spectrum (ES+) 335 (M$^+$+1).

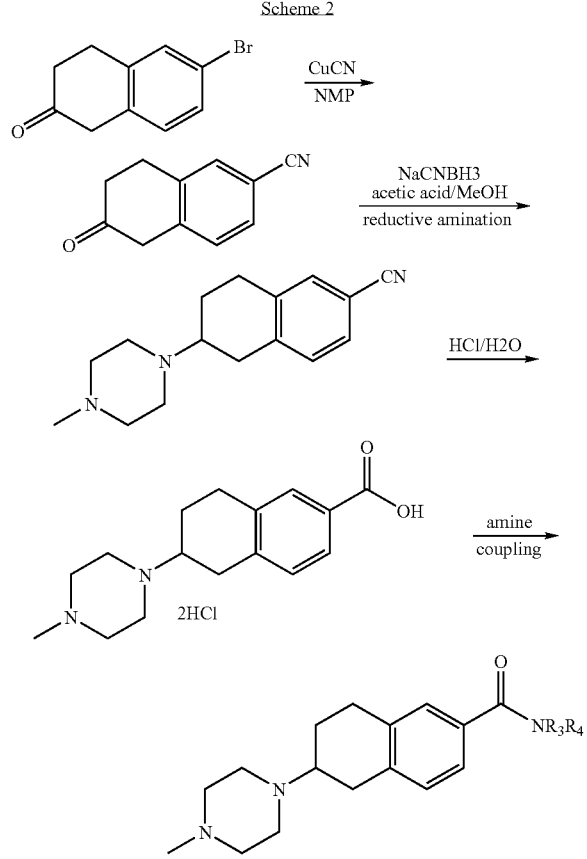

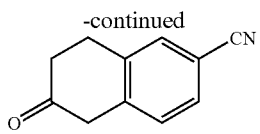

Preparation 2

Synthesis of 6-Oxo-5,6,7,8-tetrahydro-naphthalene-2-carbonitrile

See also generally Org. Prep. Proced. Int. Vol. 32, No. 1, 2000, p. 88. Charged 50 mL round bottom flask with copper (I) cyanide (1.34 g., 0.0150 moles, 1.12 eq.), 6-bromo-2-tetraline (3.0 g., 1.33 mmoles, 1.0 eq.) and 13 mL N-methylpyrrolidinone. Heated for 5 hours at 180-200° C. Allowed reaction mixture to stir at room temperature over the weekend. Transferred reaction mixture to 250 mL 3-necked, round bottomed flask fitted with a mechanical stirrer, a condenser, and an addition funnel. Added 6.0 g. Celite® and heated with stirring to 80° C. Added 70 mL water and 90 mL ethyl acetate to hot stirring reaction mixture. Turned off heat and allowed to cool overnight with stirring. The next day, filtered the reaction mixture through a Celite® pad. Partitioned off water layer from filtered reaction mixture. Washed ethyl acetate layer with water once, then washed with a 50:50 mixture of brine and water twice. Dripped organic layer through sodium sulfate to dry and removed solvents under reduced pressure to obtain 2.67 g. of light brown solid. Purified crude material via Biotage FLASH 40 L® cartridge (175 g. of silica gel) using an ethylacetate:hexane stepwise gradient. Obtained 1.77 g. (yield=78%). Product was not completely pure, but used it as is in the next reaction. H-NMR (CDCL3): 7.55 (1H, s), 7.53 (1H, d), 3.64 (2H, s), 3.12 (1H, t, J=7 Hz), 2.58 (1H, t, J=7 Hz.

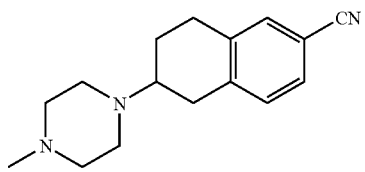

Preparation 3

Synthesis of 6-(4-Methyl-piperazin-1-yl)-5,6,7,8-tetrahydro-naphthalene-2-carbonitrile Added 100 mL toluene and 10 mL ethyl ether to 6-oxo-5,6,7,8-tetrahydro-naphthalene-2-carbonitrile (1.77 g., 10.3 mmoles., 1.0 eq.) and N-methyl piperazine (1.24 g., 12.4 mmoles, 1.2 eq.). Added 4.3 g. 4A molecular sieves to the reaction mixture and stirred at room temperature for 1.5 hours. Heated reaction mixture to 55° C. for 1 hour. NMR of reaction mixture sample indicates starting material still present. Added another 0.8 eq. of N-methyl piperazine (8.2 mmoles., 0.82 g., 0.91 mL) to the reaction mixture and stirred at room temperature overnight. The next morning, an NMR of a reaction mixture sample showed only a small amount of starting material. Filtered off the molecular sieves with filter paper and removed solvent under reduced pressure.

Added 60 mL. 10% acetic acid:methanol solution and sodium cyanoborohydride (1.92 g., 30.5 moles, 3.0 eq.) to reaction mixture. Allowed reaction mixture to stir at room temperature over the weekend. Removed solvents under reduced pressure and partitioned the reaction mixture between methylene chloride and 2.0 N sodium carbonate solution. Collected organic layer and extracted aqueous two more time with methylene chloride. Combined organic extracts and dripped through sodium sulfate to dry. Removed solvent via reduced pressure to obtain 1.84 g. of brown oil.

Partitioned between 1.0N aqueous hydrochloric acid and 1:1 ethylacetate:ethylether. Collected acid layer and extracted organic layer two more times with 1.0N aqueous hydrochloric solution. Combined acid washes and extracted two times with ethylether. Discarded the ethylether extracts. Basified the aqueous layer with 5.0 N aqueous sodium hydroxide solution. Extracted aqueous four times with ethyl acetate. Dried combined ethylacetate extracts over sodium sulfate and removed solvents via reduced pressure to obtain 0.95 g. of a brown oil. Passed this through a 10 g. Varian® silica gel cartridge using 5% (2N ammonia in methanol):methylene chloride solvent system as an eluant. Obtained 0.892 g of a brown oil (yield=34%). Not completely pure, but used as is in next reaction. Mass spectrum (APCI): 256 (M$^+$+1).

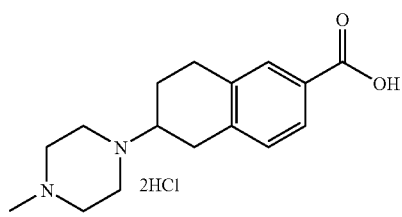

Preparation 4

Synthesis of 6-(4-methyl-piperazin-1-yl)-5,6,7,8-tetrahydro-naphthalene-2-carboxylic acid dihydrochloride Charged 100 mL round bottomed flask with 6-(4-Methyl-piperazin-1-yl)-5,6,7,8-tetrahydro-naphthalene-2-carbonitrile (0.791 g., 3.10 mmoles.), 9.0 mL water, and 11.0 mL concentrated hydrochloric acid. Heated reaction mixture with a 100-110° C. oil bath overnight. Allowed to cool to room temperature and filtered off the solid with a fretted funnel washing with water. Dried the solid in a vacuum oven at 75° C. overnight. Obtained 0.4945 g. Took mother liquors and removed some of the water via reduced pressure, stored in the refrigerator for several weeks and collected a second crop of solid via vacuum filtration. Washed second crop with water and dried in vacuum oven at 75° C. overnight. Obtained another 0.2838 g. Combining the two crops of desired product gave 0.7783 g. (yield=72%). Mass spectrum (APCI): 275 (M$^+$+1)

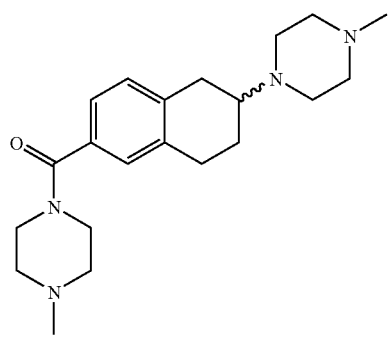

Example 8

Synthesis of (4-Methyl-piperazin-1-yl)-[6-(4-methyl-piperazin-1-yl)-5,6,7,8-tetrahydro-naphthalen-2-yl]-methanone Procedure B: Charged 4.0 mL glass vial with 6-(4-methyl-piperazin-1-yl)-5,6,7,8-tetrahydro-naphthalene-2-carboxylic acid dihydrochloride (75.0 mg, 0.216 mmoles, 1.3 eq.), 2.0 mL methylene chloride, N-methyl piperazine (16.6 mg., 0.166 mmoles, 0.0184 mL, 1.00 eq.), and triethylamine (43.7 mg., 0.432 mmoles, 2.6 eq.). Added N-cyclohexyl carbodiimide N-methyl polystyrene HL (Novabiochem, loading=1.92 mmoles/g, >0.172 g., >0.332 mmoles, >2.0 eq.) to the reaction mixture. Rotated reaction vial at room temperature overnight. The next day, filtered off resin washing alternately with methylene chloride and methanol. Purified using a Biotage FLASH 25+M® cartridge (55 g. silica gel) and eluting with a (2N NH3 in MeOH):CH$_2$Cl$_2$ stepwise gradient. Obtained 51.5 mg. (yield=87%). Mass Spectrum (APCI): 357 (M$^+$+1).

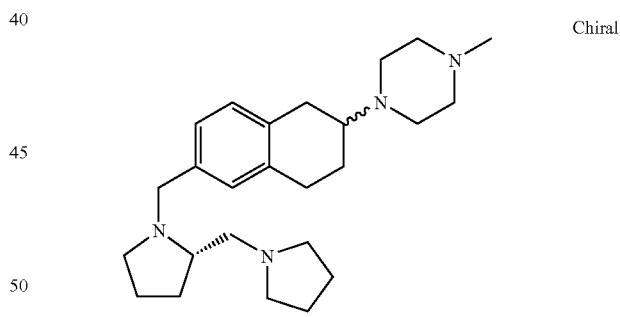

Example 9

Synthesis of 1-Methyl-4-[6-(2-pyrrolidin-1-yl)-5,6,7,8-tetrahydro-naphthalen-2-yl]-(2-pyrrolidin-1-ylmethyl-pyrrolidin-1-yl)-methanone All operations performed under nitrogen. Charged 5 mL round bottomed flask with [6-(4-methyl-piperazin-1-yl)-5,6,7,8-tetrahydro-naphthalen-2-yl]-(2-pyrrolidin 1-ylmethyl-pyrrolidin-1-yl)-methanone (51.5 mg., 0.125 mmoles., 1.0 eq.) (See herein example 13) and 1.0 mL anhydrous THF. Added 0.63 mL of 1.0 M lithium aluminum hydride in THF to the reaction mixture. Refluxed the reaction for 5 hours. Allowed to stir at room temperature for several days. Added.

0.25 mL water, 0.25 mL 5N sodium hydroxide, and 0.75 mL water. Filtered reaction mixture through a pad of Celite® and removed solvents under reduced pressure to obtain 82.7 mg. Purified crude material using a Biotage FLASH 25+S® cartridge (27 g. of silica gel) and a step wise (2N ammonia in methanol):methylene chloride solvent gradient. Obtained 19.6 mg. (yield=39%). Mass spectrum (APCI): 397 (M$^+$+1).

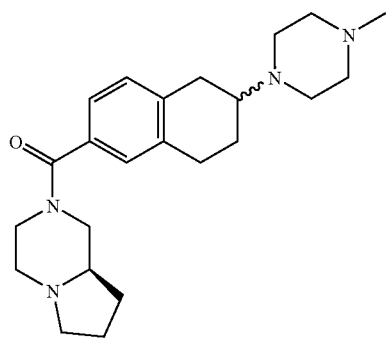

Example 10

(Hexahydro-pyrrolo[1,2-a]pyrazin-2-yl)-[6-(4-methyl-piperazin-1-yl)-5,6,7,8-tetrahydro-naphthalen-2-yl]-methanone is prepared from 6-(4-methyl-piperazin-1-yl)-5,6,7,8-tetrahydro-naphthalene-2-carboxylic acid dihydrochloride and Octahydro-pyrrolo[1,2-a]pyrazine in a manner substantially analogous to Procedure B (See herein Example 8). Observed mass 383 (M$^+$+1).

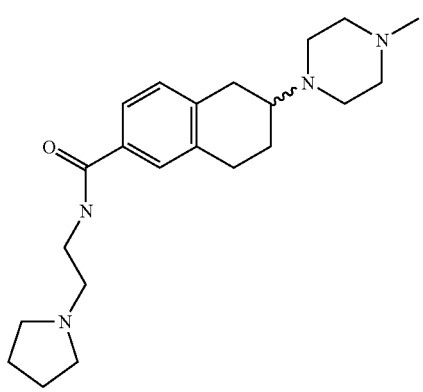

Example 11

6-(4-Methyl-piperazin-1-yl)-5,6,7,8-tetrahydro-naphthalene-2-carboxylic acid (2-pyrrolidin-1-yl-ethyl)-amide is prepared from 6-(4-methyl-piperazin-1-yl)-5,6,7,8-tetrahydro-naphthalene-2-carboxylic acid dihydrochloride and N-(2-aminoethyl)pyrrolidine in a manner substantially analogous to Procedure B (See herein Example 8). Observed mass 371 (M$^+$+1).

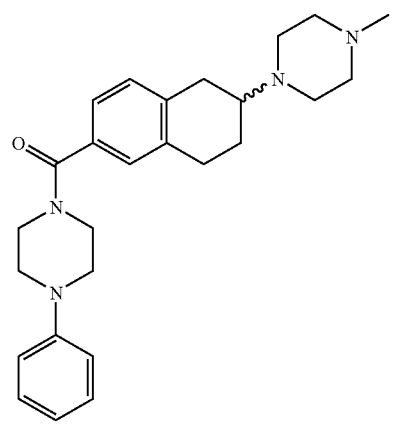

Example 12

[6-(4-Methyl-piperazin-1-yl)-5,6,7,8-tetrahydro-naphthalen-2-yl]-(4-phenyl-piperazin-1-yl)-methanone is prepared from 6-(4-methyl-piperazin-1-yl)-5,6,7,8-tetrahydro-naphthalene-2-carboxylic acid dihydrochloride and 1-phenyl-piperazine in a manner substantially analogous to Procedure B (See herein Example 8). Observed mass 419 (M$^+$+1).

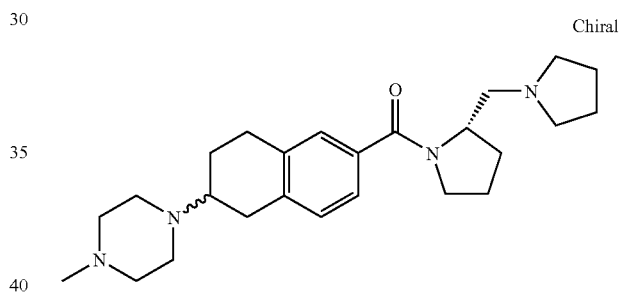

Example 13

Synthesis of [6-(4-methyl-piperazin-1-yl)-5,6,7,8-tetrahydro-naphthalen-2-yl]-(2-pyrrolidin-1-ylmethyl-pyrrolidin-1-yl)-methanone Procedure C: Charged 25 mL round bottomed flask with 6-(4-methyl-piperazin-1-yl)-5,6,7,8-tetrahydro-naphthalene-2-carboxylic acid dihydrochloride (0.250 g., 0.720 mmoles., 1.00 eq.), 10 mL methylene chloride, (S)-(+)-1-(2-pyrrolidinylmethyl)-pyrrolidine (0.111 g., 0.720 mmoles., 1.0 eq.), 1-hydroxy-7-azabenzotrizole (0.0980 g., 0.720 mmoles., 1.00 eq.), and N-ethylmorpholine (0.166 g., 1.44 mmoles., 2.00 eq.). Added 1-(3-dimethylaminopropyl)-3-ethylcarbodiimide hydrochloride (0.145 g., 0.756 mmoles., 1.05 eq.). Stirred at room temperature overnight. The next day, removed solvents via reduced pressure. Partitioned reaction mixture between methylene chloride and saturated sodium bicarbonate solution. Extracted two more times with methylene chloride. Combined organic extracts and washed with water three times and with brine one time. Removed solvents via reduced pressure to obtain 0.124 g. Purified using Biotage FLASH 25 M® silica gel cartridge (55 g. of silica gel) and eluting with 5% (2N ammonia in methanol):methylene chloride. Obtained 96.2 mg. (yield=32%) of desired product. Mass spectrum (APCI): 411 (M$^+$+1).

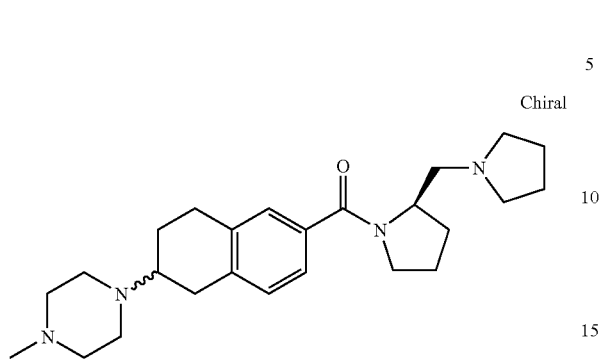

Example 14

[6-(4-methyl-piperazin-1-yl)-5,6,7,8-tetrahydro-naphthalen-2-yl]-(2-pyrrolidin-1-ylmethyl-pyrrolidin-1-yl)-methanone is prepared from 6-(4-methyl-piperazin-1-yl)-5,6,7,8-tetrahydro-naphthalene-2-carboxylic acid dihydrochloride and (R)-(+)-1-(2-pyrrolidinylmethyl)-pyrrolidine in a manner substantially analogous to Procedure C (See herein Example 13). Observed mass 411 (M$^+$+1).

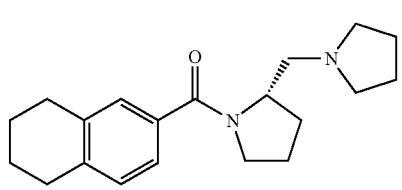

Example 15

Synthesis of (S)-(2-Pyrrolidin-1-ylmethyl-pyrrolidin-1-yl)-(5,6,7,8-tetrahydro-naphthalen-2-yl)-methanone Procedure D: Charged 8 mL glass vial with 5,6,7,8-tetrahydro-2-naphthoic acid (150 mg., 0.851 mmoles., 1.2 eq.), 6 mL of 5:1:1 chloroform:acetonitrile:t-butanol, (S)-(+)-1-(2-pyrrolidinylmethyl)pyrrolidine (109 mg., 0.709 mmoles., 1.0 eq.) and 1-hydroxybenzotriazole hydrate (143.8 mg., 1.06 mmoles, 1.5 eq.). Added N-cyclohexylcarbodiimide N'-methylpolystyrene HL (0.739 g., loading=1.92 mmoles/g., 2.0 eq.). Capped vial and rotated for two days. Added Tris-(2-aminoethyl)amine polystyrene (0.817 g., loading=4.34 mmoles/g., 5.0 eq.) and rotated reaction vial for several hours. Filtered off resin and concentrated under a stream of nitrogen. Purified crude material using a Biotage FLASH 40+M® cartridge (100 g. of silica gel) and a (2N ammonia in methanol): methylene chloride solvent system. Collected 189.6 mg. (yield=85%). Mass spectrum (APCI): 313 (M$^+$+1).

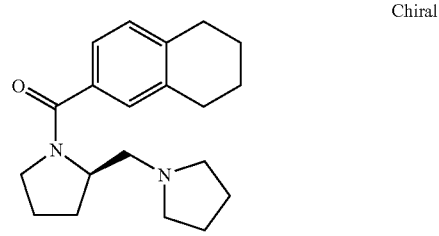

Example 16

(R)-(2-Pyrrolidin-1-ylmethyl-pyrrolidin-1-yl)-(5,6,7,8-tetrahydro-naphthalen-2-yl)-methanone is prepared from (R)-(+)-1-(2-pyrrolidinylmethyl)-pyrrolidine in a manner substantially analogous to Procedure D (See herein Example 15). Observed mass 313 (M$^+$+1).

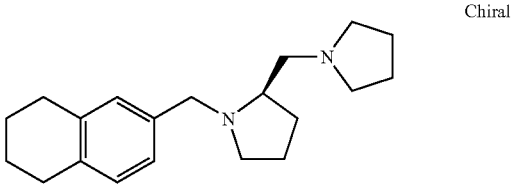

Example 17

(S)-(2-pyrrolidin-1-ylmethyl-pyrrolidin-1-yl)-(5,6,7, 8-tetrahydro-naphthalen-2-yl)-methane Procedure E: All operations performed under nitrogen. Charged round bottomed flask with (S)-(2-pyrrolidin-1-ylmethyl-pyrrolidin-1-yl)-(5,6,7,8-tetrahydro-naphthalen-2-yl)-methanone (100 mg., 0.348 mmoles, 1.0 eq.) and 2.0 mL anhydrous tetrahydrofuran. Added 0.6 mL 1M lithium aluminum hydride in tetrahydrofuran (0.576 mmoles, 1.8 eq.) and heated at reflux for several hours. Allowed to stir at room temperature over the weekend. Added 2.0 g. of sodium sulfate decahydrate (Aldrich) and allowed to stir for several hours. Filtered the reaction mixture through a Celite® pad and removed solvents under reduced pressure. Obtained a crude yield of 0.1966 g. Purified crude with Biotage FLASH 25+S® cartridge (20 g. of silica gel) and a step wise (2N ammonia in methanol):methylene chloride solvent gradient. Recovered 47.3 mg. (yield=49%). Mass spectrum (APCI): 299 (M$^+$+1)

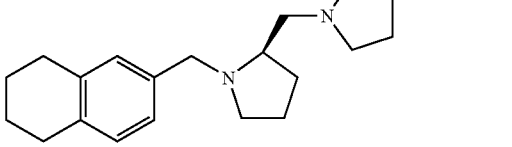

Example 18

(R)-(2-pyrrolidin-1-ylmethyl-pyrrolidin-1-yl)-(5,6,7,8-tetrahydro-naphthalen-2-yl)-methane is prepared from (R)-

(2-Pyrrolidin-1-ylmethyl-pyrrolidin-1-yl)-(5,6,7,8-tetrahydro-naphthalen-2-yl)-methanone in a manner substantially analogous to Procedure E (See herein Example 17). Observed mass 299 (M++1).

TABLE 1

| Example Number | Structure |
|---|---|
| 1 | 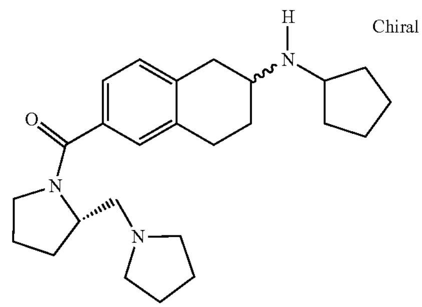 |
| 2 | 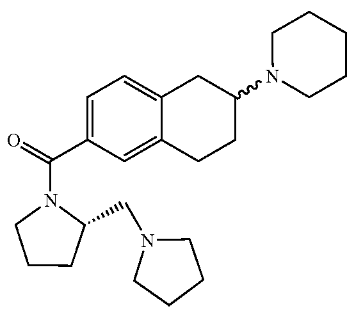 |
| 3 | 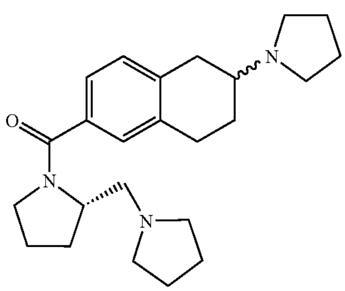 |
| 4 | 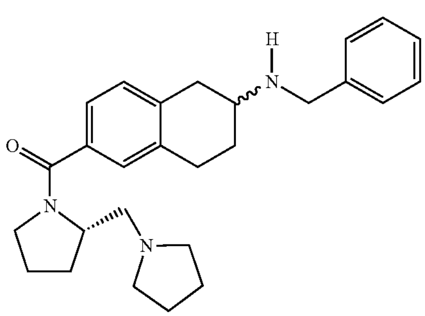 |
| 5 | |
| 6 | |
| 7 | |
| 8 | |

TABLE 1-continued
| Example Number | Structure |
|---|---|
| 9 | 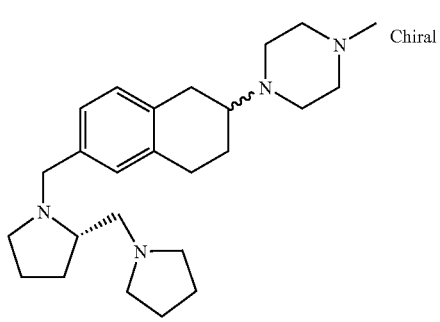 Chiral |
| 10 | 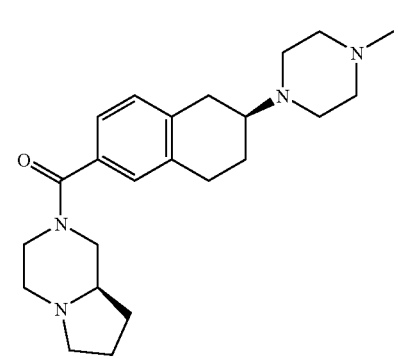 |
| 11 | 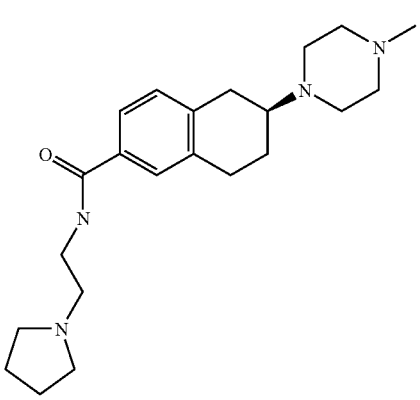 |
| 12 | 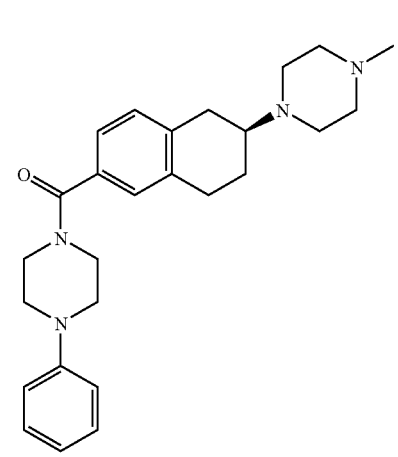 |
| 13 | 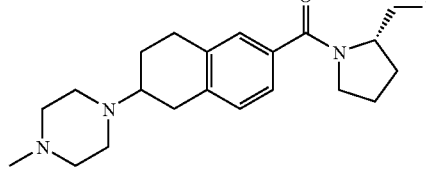 Chiral |
| 14 | 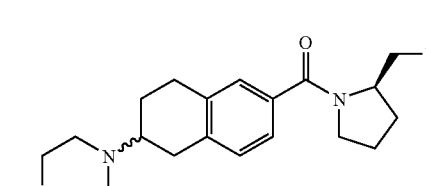 Chiral |
| 15 | 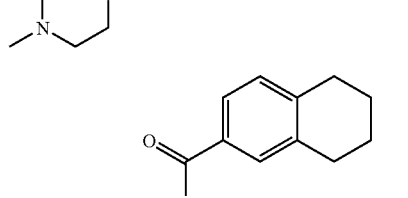 |
| 16 | 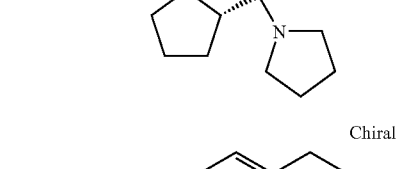 Chiral |
| 17 | 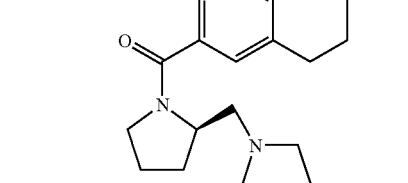 Chiral |
| 18 | 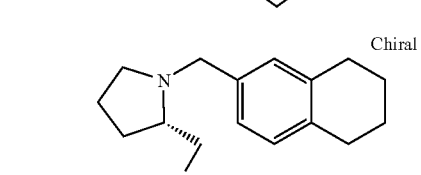 Chiral |
The pharmaceutical salts of the invention are typically formed by reacting a compound of Formula I or II or III with an equimolar or excess amount of acid or base. The reactants are generally combined in a mutual solvent such as diethylether, tetrahydrofuran, methanol, ethanol, isopropanol, benzene, and the like for acid addition salts, or water, an alcohol or a chlorinated solvent such as dichloromethane for base addition salts. The salts normally precipitate out of solution within about one hour to about ten days and can be isolated by filtration or other conventional methods.

Acids commonly employed to form pharmaceutical acid addition salts are inorganic acids such as hydrochloric acid, hydrobromic acid, hydroiodic acid, sulfuric acid, phosphoric acid, and the like, and organic acids such as p-toluenesulfonic, methanesulfonic acid, ethanesulfonic acid, oxalic acid, p-bromophenylsulfonic acid, carbonic acid, succinic acid, citric acid, tartaric acid, benzoic acid, acetic acid, and the like. Preferred pharmaceutical acid addition salts are those formed with mineral acids such as hydrochloric acid, hydrobromic acid, and sulfuric acid, and those formed with organic acids such as maleic acid, tartaric acid, and methanesulfonic acid.

Bases commonly employed to form pharmaceutical base addition salts are inorganic bases, such as ammonium or alkali or alkaline earth metal hydroxides, carbonates, bicarbonates, and the like. Such bases useful in preparing the salts of this invention thus include sodium hydroxide, potassium hydroxide, ammonium hydroxide, potassium carbonate, sodium carbonate, sodium bicarbonate, potassium bicarbonate, calcium hydroxide, calcium carbonate, and the like. The potassium and sodium salt forms are particularly preferred.

It should be recognized that the particular counterion forming a part of any salt of this invention is not of a critical nature, so long as the salt as a whole is pharmacologically acceptable and as long as the counterion does not contribute undesired qualities to the salt as a whole.

The optimal time for performing the reactions of the Schemes and the Route can be determined by monitoring the progress of the reaction via conventional chromatographic techniques. Furthermore, it is preferred to conduct the reactions of the invention under an inert atmosphere, such as, for example, argon, or, particularly, nitrogen. Choice of solvent is generally not critical so long as the solvent employed is inert to the ongoing reaction and sufficiently solubilizes the reactants to effect the desired reaction. The compounds are preferably isolated and purified before their use in subsequent reactions. Some compounds may crystallize out of the reaction solution during their formation and then collected by filtration, or the reaction solvent may be removed by extraction, evaporation, or decantation. The intermediates and final products of Formula I or II or III may be further purified, if desired by common techniques such as recrystallization or chromatography over solid supports such as silica gel or alumina.

The skilled artisan will appreciate that not all substituents are compatible with all reaction conditions. These compounds may be protected or modified at a convenient point in the synthesis by methods well known in the art.

The compound of Formula I or II or III is preferably formulated in a unit dosage form prior to administration. Therefore, yet another embodiment of the present invention is a pharmaceutical composition comprising a compound of Formula I or II or III and one or more pharmaceutically acceptable carriers, diluents or excipients.

The present pharmaceutical compositions are prepared by known procedures using well-known and readily available ingredients. In making the formulations of the present invention, the active ingredient (Formula I or II or III compound) will usually be mixed with a carrier, or diluted by a carrier, or enclosed within a carrier which may be in the form of a capsule, sachet, paper or other container. When the carrier serves as a diluent, it may be a solid, semisolid or liquid material that acts as a vehicle, excipient, or medium for the active ingredient. Thus, the compositions can be in the form of tablets, pills, powders, lozenges, sachets, cachets, elixirs, suspensions, emulsions, solutions, syrups, aerosol (as a solid or in a liquid medium), soft and hard gelatin capsules, suppositories, sterile injectable solutions and sterile packaged powders.

Some examples of suitable carriers, excipients, and diluents include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water syrup, methyl cellulose, methyl and propylhydroxybenzoates, talc, magnesium stearate and mineral oil. The formulations can additionally include lubricating agents, wetting agents, emulsifying and suspending agents, preserving agents, sweetening agents or flavoring agents. The compositions of the invention may be formulated so as to provide quick, sustained or delayed release of the active ingredient after administration to the patient.

The compositions of the present invention may be formulated in sustained release form to provide the rate controlled release of any one or more of the components or active ingredients to optimize the therapeutic effects, i.e., antihistaminic activity and the like. Suitable dosage forms for sustained release include layered tablets containing layers of varying disintegration rates or controlled release polymeric matrices impregnated with the active components and shaped in tablet form or capsules containing such impregnated or encapsulated porous polymeric matrices.

Liquid form preparations include solutions, suspensions and emulsions. As an example may be mentioned water or water-propylene glycol solutions for parenteral injections or addition of sweeteners and opacifiers for oral solutions, suspensions and emulsions. Liquid form preparations may also include solutions for intranasal administration.

Aerosol preparations suitable for inhalation may include solutions and solids in powder form, which may be in combination with a pharmaceutically acceptable carrier such as inert compressed gas, e.g. nitrogen.

For preparing suppositories, a low melting wax such as a mixture of fatty acid glycerides such as cocoa butter is first melted, and the active ingredient is dispersed homogeneously therein by stirring or similar mixing. The molten homogeneous mixture is then poured into convenient sized molds, allowed to cool and thereby solidify.

Also included are solid form preparations which are intended to be converted, shortly before use, to liquid form preparations for either oral or parenteral administration, Such liquid forms include solutions, suspensions and emulsions.

The compounds of the invention may also be deliverable transdermally. The transdermal compositions may take the form of creams, lotions, aerosols and/or emulsions and can be included in a transdermal patch of the matrix or reservoir type as a re conventional in the art for this purpose.

Preferably the compound is administered orally.

Preferably, the pharmaceutical preparation is in a unit dosage form. In such form, the preparation is subdivided into suitably sized unit doses containing appropriate quantities of the active components, e.g., an effective amount to achieve the desired purpose.

The quantity of the inventive active composition in a unit dose of preparation may be generally varied or adjusted from about 0.01 milligrams to about 1,000 milligrams, preferably from about 0.01 to about 950 milligrams, more preferably from about 0.01 to about 500 milligrams, and typically from about 1 to about 250 milligrams, according to the particular application. The actual dosage employed may be varied depending upon the patient's age, sex, weight and severity of the condition being treated. Such techniques are well known to those skilled in the art. Generally, the human oral dosage form containing the active ingredients can be administered 1 or 2 times per day.

Utility

Compounds of Formula I or II or III are effective as histamine H3 receptor antagonists or inverse agonists. More particularly, these compounds are selective histamine H3 receptor antagonists that have little or no affinity for histamine receptor GPRv53(H4R). As selective antagonists, the compounds of Formula I or II or III are useful in the treatment of diseases, disorders, or conditions responsive to the inactivation of the histamine H3 receptor, including but not limited to obesity and other eating-related disorders. It is postulated that selective antagonists of H3R will raise brain histamine levels and possibly that of other monoamines resulting in inhibition of food consumption while minimizing peripheral consequences. Although a number of H3R antagonists are known in the art, none have proven to be satisfactory obesity drugs. There is increasing evidence that histamine plays an important role in energy homeostasis. Histamine, acting as a neurotransmitter in the hypothalamus, suppressed appetite. Histamine is an almost ubiquitous amine found in many cell types and it binds to a family of G protein-coupled receptors (GPCRs). This family provides a mechanism by which histamine can elicit distinct cellular responses based on receptor distribution. Both the H1R and H2R are widely distributed. H3R is primarily expressed in the brain, notably in the thalamus and caudate nucleus. High density of expression of H3R was found in feeding center of the brain. A novel histamine receptor GPRv53 has been recently identified. GPRv53 is found in high levels in peripheral white blood cells; only low levels have been identified in the brain by some investigators while others cannot detect it in the brain. However, any drug discovery effort initiated around H3R must consider GPRv53 as well as the other subtypes.

The inventive compounds can readily be evaluated by using a competitive inhibition Scintillation Proximity Assay (SPA) based on a H3R binding assay using [3H] α methylhistamine as ligand. Stable cell lines, including but not limited to HEK can be transfected with cDNA coding for H3R to prepare membranes used for the binding assay. The technique is illustrated below (*Preparation of Histamine Receptor Subtype Membranes*) for the histamine receptor subtypes.

Membranes isolated as described in (*Preparation of Histamine Receptor Subtype Membranes*) were used in a [35S] GTP$_\gamma$S functional assay. Binding of [35S]GTP$_\gamma$S to membranes indicates agonist activity. Compounds of the invention of Formula I or II or III were tested for their ability to inhibit binding in the presence of agonists. Alternately, the same transfected cell lines were used for a cAMP assay wherein H3R agonists inhibited forskolin-activated synthesis of cAMP. Compounds of Formula I or II or III were tested for their ability to permit forskolin-stimulated cAMP synthesis in the presence of agonist.

Preparation of Histamine Receptor Subtype Membranes

A. Preparation H1R Membranes cDNA for the human histamine 1 receptor (H1R) was cloned into a mammalian expression vector containing the CMV promoter (pcDNA3.1(+), Invitogen) and transfected into HEK293 cells using the FuGENE Tranfection Reagent (Roche Diagnostics Corporation). Transfected cells were selected using G418 (500 μ/ml). Colonies that survived selection were grown and tested for histamine binding to cells grown in 96-well dishes using a scintillation proximity assay (SPA) based radioligand binding assay. Briefly, cells, representing individual selected clones, were grown as confluent monolayers in 96-well dishes (Costar Clear Bottom Plates, #3632) by seeding wells with 25,000 cells and growing for 48 hours (37° C., 5% $CO_2$). Growth media was removed and wells were rinsed two times with PBS (minus $Ca^{2+}$ or $Mg^{2+}$). For total binding, cells were assayed in a SPA reaction containing 50 mM Tris-HCL (assay buffer), pH 7.6, 1 mg wheat germ agglutinin SPA beads (Amersham Pharmacia Biotech, #RPNQ0001), and 0.8 nM $^3$H-pyrilamine (Net-594, NEN) (total volume per well ~200 μl). Astemizole (10 μM, Sigma #A6424) was added to appropriate wells to determine non-specific binding. Plates were covered with FasCal and incubated at room temperature for 120 minutes. Following incubation, plates were centrifuged at 1,000 rpm (~800 g) for 10 minutes at room temperature. Plates were counted in a Wallac Trilux 1450 Microbeta scintillation counter. Several clones were selected as positive for binding, and a single clone (H1R40) was used to prepare membranes for binding studies. Cell pellets, representing ~10 grams, were resuspended in 30 ml assay buffer, mixed by vortexing, and centrifuged (40,000 g at 4° C.) for 10 minutes. The pellet resuspension, vortexing, and centrifugation was repeated 2 more times. The final cell pellet was resuspended in 30 ml and homogenized with a Polytron Tissue Homogenizer. Protein determinations were done using the Coomassie Plus Protein Assay Reagent (Pierce). Five micrograms of protein was used per well in the SPA receptor-binding assay.

B. Preparation H2R Membranes cDNA for the human histamine 2 receptor was cloned, expressed and transfected into HEK 293 cells as described above. Histamine binding to cells was assayed by SPA described above. For total binding, cells were assayed in a SPA reaction containing 50 mM Tris-HCl (assay buffer), pH 7.6, 1 mg wheat germ agglutinin SPA beads (Amersham Pharmacia Biotech, #RPNQ0001), and 6.2 nM $^3$H-tiotidine (Net-688, NEN) (total volume per well=200 μl). Cimetidine (10 μM, Sigma #C4522) was added to appropriate wells to determine non-specific binding.

Several clones were selected as positive for binding, and a single clone (H2R10) was used to prepare membranes for binding studies. Five micrograms of protein was used per well in the SPA receptor-binding assay.

C. Preparation of H3R Membranes cDNA for the human histamine 3 receptor was cloned and expressed as described in (A. Preparation H1R membranes), above. Transfected cells were selected using G418 (500 μ/ml), grown, and tested for histamine binding by the SPA described above. For total binding, cells were assayed in a SPA reaction described above containing 50 mM Tris-HCL (assay buffer), pH 7.6, 1 mg wheat germ agglutinin SPA beads (Amersham Pharmacia Biotech, #RPNQ0001), and 1 nM (3H)-n-alpha-methylhistamine (NEN, NET1027) (total volume per well=200 μl). Thioperimide was added to determine non-specific binding. Several clones were selected as positive for binding, and a single clone (H3R8) was used to prepare membranes for binding studies described above. Five micrograms of protein was used per well in the SPA receptor-binding assay.

All compounds set forth in the examples exhibited affinity for the H3 receptor greater than 1 uM. Preferred compounds of the invention exhibited affinity for the H3 receptor greater than 200 nM. Most preferred compounds of the invention exhibit affinity for the H3 receptor greater than 20 nM.

D. Preparation of GPRv53 Membranes cDNA for the human GPRv53 receptor was cloned and expressed as described in (A. Preparation H1R membranes), above. Transfected cells were selected, tested for histamine binding, and selected. HEK293 GPRv53 50 cells were grown to confluency in DMEM/F12 (Gibco) supplemented with 5% FBS and 500 ug/ml G418 and washed with Delbecco's PBS (Gibco) and harvested by scraping. Whole cells were homogenized with a Polytron tissuemizer in binding buffer, 50 mM Tris pH 7.5. Cell lysates, 50 ug, were incubated in 96 well dishes with 3 nM (3H) Histamine and compounds in binding buffer for 2 hours at room temperature. Lysates were filtered through glass fiber filters (Perkin Elmer) with a Tomtec cell harvester. Filters were counted with melt-on scintillator sheets (Perkin Elmer) in a Wallac Trilux 1450 Microbeta Scintillation counter for 5 minutes.

Pharmacological Results cAMP ELISA

HEK293H3R8 cells prepared as described above were seeded at a density of 50,000 cells/well and grown overnight in DMEM/F12 (Gibco) supplemented with 5% FBS and 500 ug/ml G418. The next day tissue culture medium was removed and replaced with 50 µl cell culture medium containing 4 mM 3-isobutyl-1-methylxanthine (Sigma) and incubated for 20 minutes at room temperature. Antagonist were added in 50 µl cell culture medium and incubated for 20 minutes at room temperature. Agonist R (−)α methylhistamine (RBI) at a dose response from $1\times10^{-10}$ to $1\times10^{-5}$ M was then added to the wells in 50 µl cell culture medium and incubated for 5 minutes at room temperature. Then 50 µl of cell culture medium containing 20 µM Forskolin (Sigma) was added to each well and incubated for 20 minutes at room temperature. Tissue culture medium was removed and cells were lysed in 0.1M HCl and cAMP was measured by ELISA (Assay Designs, Inc.).

[35S] GTP γ[S] Binding Assay

Antagonist activity of selected compounds was tested for inhibition of [35S] GTP γ[S] binding to H3R membranes in the presence of agonists. Assays were run at room temperature in 20 mM HEPES, 100 mM NaCl, 5 mM $MgCl_2$ and 10 uM GDP at pH 7.4 in a final volume of 200 ul in 96-well Costar plates. Membranes isolated from H3R8-expressing HEK293 cell line (20 ug/well) and GDP were added to each well in a volume of 50 µl assay buffer. Antagonist was then added to the wells in a volume of 50 µl assay buffer and incubated for 15 minutes at room temperature. Agonist R(−) alpha methylhistamine (RBI) at either a dose response from $1\times10^{-10}$ to $1\times10^{-5}$ M or fixed concentration of 100 nM were then added to the wells in a volume of 50 µl assay buffer and incubated for 5 minutes at room temperature. GTPγ[35S] was added to each well in a volume of 50 µl assay buffer at a final concentration of 200 µM, followed by the addition of 50 µl of 20 mg/ml WGA coated SPA beads (Amersham). Plates were counted in Wallac Trilux 1450 Microbeta scintillation counter for 1 minute. Compounds that inhibited more than 50% of the specific binding of radioactive ligand to the receptor were serially diluted to determine a K[i](nM). The results are given below for the indicated compound.

TABLE 2

| Example | Ki (nM) |
|---|---|
| 3 | 1.5 |
| 6 | 7.8 |

To investigate the selectivity of the antagonists for the histamine receptors, a competitive binding assay described above was performed. The ability of example 15 (structure given above) to selectively inhibit binding to H3R, H1R, H2 and H4R was determined. Importantly, the identification of H3R-specific antagonists that do not bind the newly identified H4R was demonstrated. Until the present invention, most known H3R antagonists also bound H4R. As demonstrated in Table 3, example 15 did not inhibit binding H4R compared to H3R.

TABLE 3

| | Ki (nM) | | | |
|---|---|---|---|---|
| Compound | H3R | H4R | H1R | H2 |
| Example 15 | 1.8 | ≧20,000 | ≧20,000 | ≧17,809 |

From the above description, one skilled in the art can ascertain the essential characteristics of the present invention, and without departing from the spirit and scope thereof, can make various changes and modifications of the invention to adapt it to various usages and conditions. Thus, other embodiments are also within the claims.

We claim:

1. A compound structurally represented by Formula I

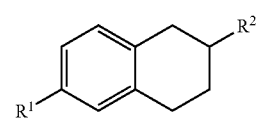

Formula (I)

or a pharmaceutically acceptable salts thereof, wherein:

$R^1$ is

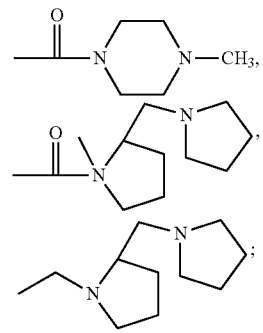

$R^2$ is

—Hydrogen, —NH—$(C_1-C_6)$ alkyl,

—NH—$(C_1-C_4)$ alkylene-phenyl, —NH$(C_3-C_6)$cycloakyl,

—$NR^3R^4$,

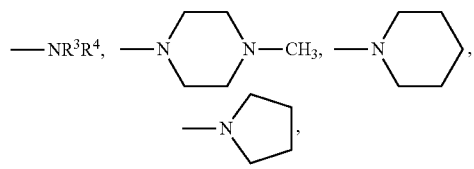

wherein;

R³ is hydrogen,
  —(C₁-C₄) alkyl,

R⁴ is
  —(C₁-C₄) alkyl,
  —(C₁-C₄) alkylene-phenyl, wherein R³ and R⁴ can cyclize to form, together with the nitrogen to which they are attached, a five or six-membered ring, wherein optionally one of the carbons of the ring formed by said nitrogen, R³, and R⁴, is replaced by a nitrogen or oxygen, and wherein said ring is optionally further substituted by R⁵, and R⁵ is hydrogen,
  —(C₁-C₄) alkyl, wherein optionally R⁵ forms a 3 to five membered ring with the nitrogen containing ring to which it is attached,
  —(C₁-C₄) alkylene-N-pyrrolidinyl,
  —(C₁-C₄) alkylene-N-piperidinyl.

2. A compound of claim 1 selected from the group consisting of:

| Example Number | |
|---|---|
| 1 | 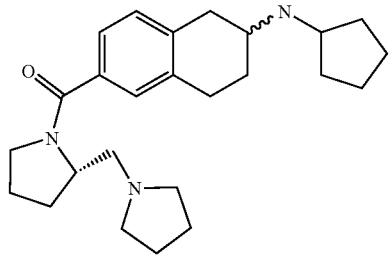 Chiral |
| 2 | 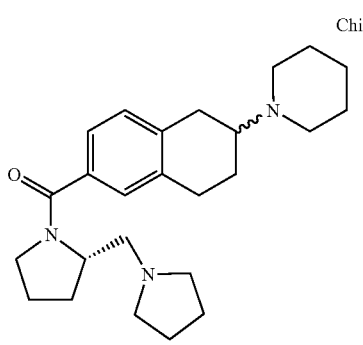 Chiral |
| 3 | 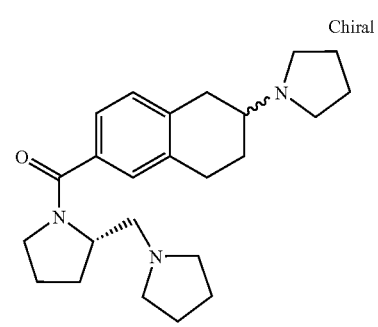 Chiral |
| 4 | 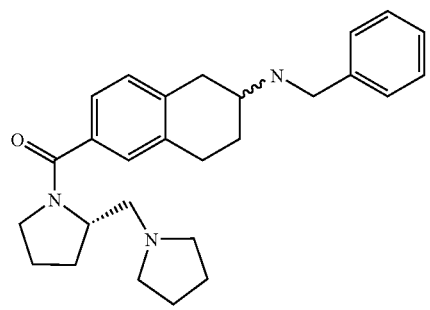 Chiral |
| 5 | 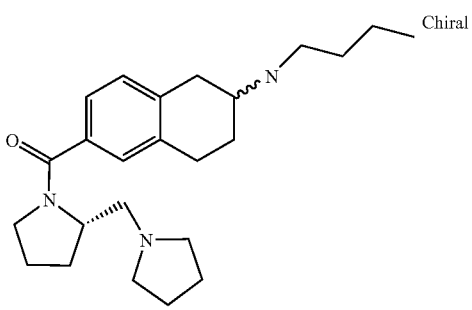 Chiral |
| 6 | 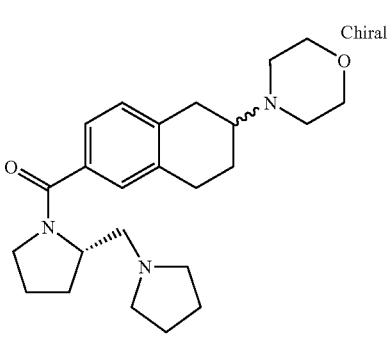 Chiral |
| 8 | 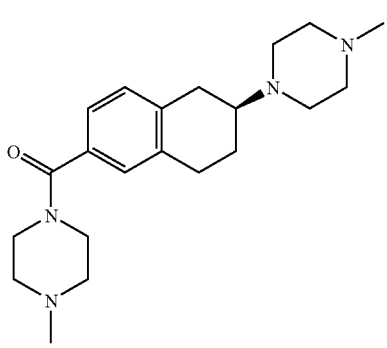 |

| Example Number | |
|---|---|
| 9 | 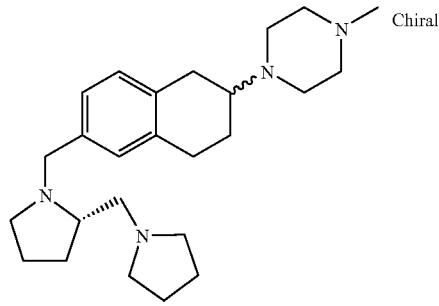 |
| 13 | 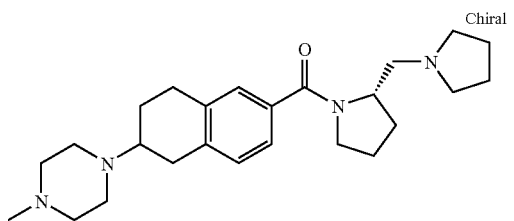 |
| 14 | 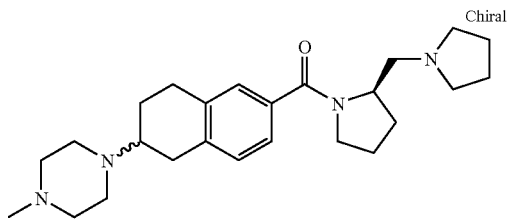 |
| 15 | 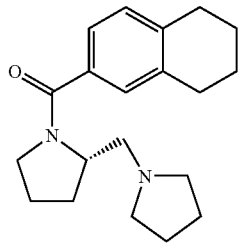 |
| Example Number | |
|---|---|
| 16 | 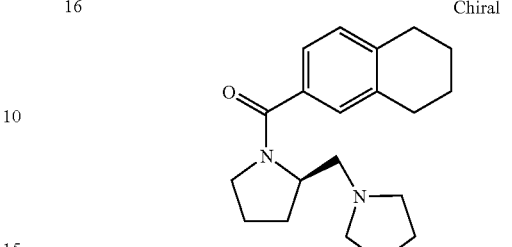 |
| 17 | 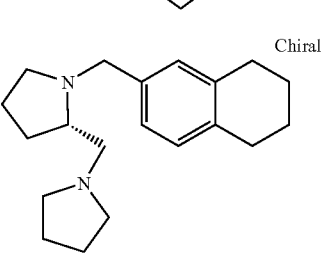 |
| 18 | 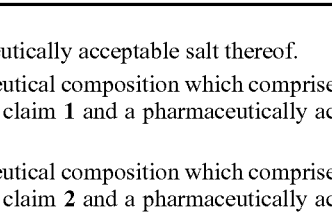 |
or a pharmaceutically acceptable salt thereof.
3. A pharmaceutical composition which comprises a compound or salt of claim 1 and a pharmaceutically acceptable carrier.
4. A pharmaceutical composition which comprises a compound or salt of claim 2 and a pharmaceutically acceptable carrier.
* * * * *